United States Patent [19]
Lodaya et al.

[11] Patent Number: 6,025,508
[45] Date of Patent: Feb. 15, 2000

[54] PREPARATION OF QUINONEDIIMINES FROM PHENYLENEDIAMINES USING OXYGEN AND A METAL OR METAL SALT CATALYST

[75] Inventors: Jayant S. Lodaya, Akron; Raymond A. Lohr, Jr., Avon; Donald L. Fields, Jr., Copley, all of Ohio

[73] Assignee: Flexsys America L.P., Akron, Ohio

[21] Appl. No.: 09/322,820

[22] Filed: May 28, 1999

Related U.S. Application Data

[60] Provisional application No. 60/087,754, Jun. 2, 1998.

[51] Int. Cl.$^7$ ..................................................... C07C 50/04
[52] U.S. Cl. ............................................................. 552/301
[58] Field of Search ................................................. 552/301

[56] References Cited

U.S. PATENT DOCUMENTS 5,053,540  10/1991  Cottman .
5,091,545   2/1992  Parker .
5,189,218   2/1993  Desmars et al. .

*Primary Examiner*—Paul J. Killos
*Attorney, Agent, or Firm*—Louis A. Morris

[57] ABSTRACT

A phenylenediamine compound can be converted, with high selectivity, into its corresponding quinonediimine by reacting the phenylenediamine with oxygen and a metal catalyst or a salt thereof.

37 Claims, No Drawings

PREPARATION OF QUINONEDIIMINES FROM PHENYLENEDIAMINES USING OXYGEN AND A METAL OR METAL SALT CATALYST

This application claims priority to the filing date of U.S. Provisional Application 60/087,754, filed Jun. 2, 1998.

FIELD OF THE INVENTION

This invention relates to a process for preparing quinonediimines from their corresponding phenylenediamines using oxygen and a metal catalyst or a salt of a metal catalyst.

BACKGROUND OF THE INVENTION

The class of cyclic enones is well known in organic chemistry. Best known examples of cyclic enones are quinones such as, for example, the benzoquinones, naphthoquinones, anthraquinones, phenanthraquinones, and the like. 1,4-Benzoquinone is commonly referred to as quinone. Quinones are generally brightly colored compounds and have versatile applications in chemical synthesis, biological uses, as redox materials, as well as in industry. There are several review articles on the chemistry and applications of quinones including, for example, *Kirk-Othmer Encyclopedia of Chemical Technology*, Third ed., Vol. 19, pages 572–605, John Wiley & Sons, New York, 1982. The synthesis of quinones is well documented. See, for example, J. Cason, *Synthesis of Benzoquinones by Oxidation*, in *Organic Synthesis*, Vol. IV, page 305, John Wiley & Sons, New York (1948). Quinones generally are prepared by oxidizing the appropriately disubstituted aromatic hydrocarbon derivatives, the substituents being hydroxyl or amino groups in the ortho or para positions. 1,4-benzoquinone, for example, can be made from the oxidation of hydroquinone, p-aminophenol or p-phenylenediamine, or from quinic acid. The reagents generally used for the oxidation are dichromate/sulfuric acid mixture, ferric chloride, silver (II) oxide or ceric ammonium nitrate. In these cases, oxidation of the aminoaromatic compound is accompanied by hydrolysis to the corresponding quinone. Some processes may take several hours for completion of the reaction.

Thus, certain prior art processes utilize a catalytic agent to achieve an acceptable reaction while other processes proceed without catalysts. The process according to the present invention utilizes a metal or metal salt oxidation catalyst which provides high conversion and reaction rates to prepare the quinonediimine.

A prior art process, which utilizes a catalyst in the preparation of a quinoneimine compound, is disclosed by Desmurs, et al. in U.S. Pat. No. 5,189,218. The process of Desmurs, et al., which converts N-(4-hydroxyphenyl)aniline into N-phenylbenzoquinone-imine, utilizes a manganese, copper, cobalt, and/or nickel compound as a catalyst in an oxidation type reaction. Although Desmurs, et al. identify converting the N-phenylbenzoquinone-imine into an N-phenyl-N'-cycloalkyl-2,5-cyclohexadine-1,4-diimine, Desmurs, et al. fails to recognize the use of an oxidation catalyst for the conversion, much less a metal oxidation catalyst, as used in the present invention. This is evidenced by Desmurs, et al. suggestion at col. 5, lines 14–22, to use a hydrogenation catalyst.

Other processes are known which use oxidizing agents to convert phenylenediamines into their corresponding quinonediimines. For example, EP 708,081 (Bernhardt et al), which describes the conversion of phenylenediamines to phenylenediimines by oxidation of the diamine in an alkali/alcoholic solution, gives a general description of such processes in its background. The EP '081 process suffers from various disadvantages including long reaction times and low yields.

Additional oxidation conversion processes are described by Wheeler in U.S. Pat. No. 5,118,807, by GB1,267,635 and by Haas et al, in EP 708,080. However, the use of oxygen along with a metal catalyst or salt of a metal catalyst in the conversion of phenylenediamine compounds to give highly selective yields of quinonediimine compounds has not heretofore been suggested.

As such, the current invention is based on the problem of providing a simple and economic process for the preparation of quinonediimines in high yields and with high purity.

SUMMARY OF THE INVENTION

It has been discovered that phenylenediamine compounds can be converted with extremely high selectivity into the corresponding quinonediimine by reaction of the diamine with metal catalyst, or a salt thereof, in the presence of oxygen. Conditions are revealed in which nearly quantitative yields have been obtained.

In contrast to prior art, an advantage of the present invention is that the conversion of phenylenediamine to the corresponding quinonediimine is nearly quantitative. Thus, very little waste material remains upon completion of the reaction.

An additional advantage is that the metal or metal salt catalytic agent, as set forth herein, provide an extremely high conversion, high selectivity and faster more complete reaction compared to prior art processes.

Still further advantages of the present invention will become apparent to those skilled in the art upon reading and understanding the following detailed description of the preferred embodiments.

DETAILED DESCRIPTION OF THE INVENTION

The object of the present invention is to provide an effective process for converting phenylenediamines into their corresponding quinonediimines.

In accordance with the object of the invention, a phenylenediamine (ortho or para) according to Formula Ia or Ib:

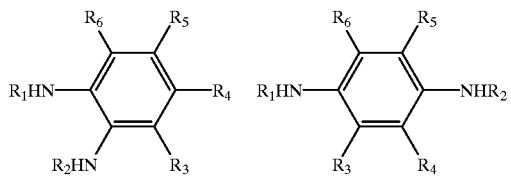

wherein $R_1$ and $R_2$ are independently selected from hydrogen, hydroxyl, alkyl, alkoxy, aryloxy, alkenyl, cycloalkyl, aryl, aralkyl, alkaryl, alkylamino, arylamino, heterocycle, acyl, formyl, aroyl, cyano, halogen, thiol, alkylthio, arylthio, amino, nitro, sulfonate, alkyl sulfonyl, aryl sulfonyl, amino sulfonyl, hydroxy carbonyl, alkyloxycarbonyl and aryloxycarbonyl, wherein the alkyl moieties in the $R_1$ and $R_2$ groups may be linear or branched and each of the $R_1$ and $R_2$ groups may be further substituted; further wherein $R_3$, $R_4$, $R_5$, and $R_6$ are the same or different and are selected from hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, alkylthio, arylthio, amino, nitro, sulfonate, alkyl sulfonyl, aryl sulfonyl, aminosulfonyl, hydroxycarbonyl, alkyloxycarbonyl and aryloxycarbonyl, wherein the alkyl moieties in the $R_3$, $R_4$, $R_5$, and $R_6$ groups may be linear or branched and each of the $R_3$, $R_4$, $R_5$, and $R_6$ groups may be further substituted where appropriate; is reacted with oxygen in the presence of a metal catalyst or salt thereof.

The reaction produces a corresponding quinonediimine according to Formula IIa or IIb:

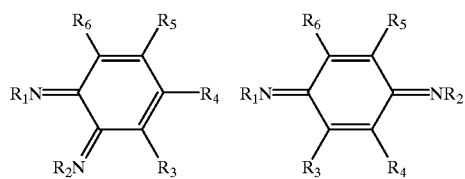

wherein $R_1$, $R_2$, $R_3$, $R_4$, $R_5$, and $R_6$ are the same as in the compound according to Formula Ia or Ib.

The reaction is represented as follows:

Reaction Scheme 1

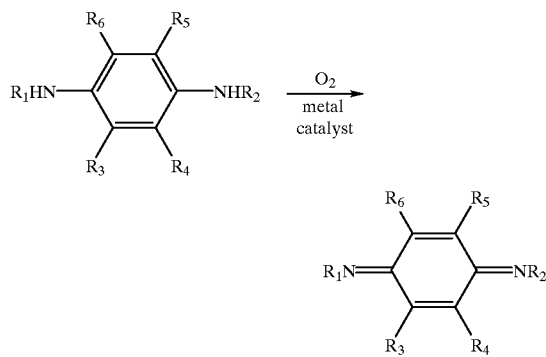

More particularly, the $R_1$ and $R_2$ variables are selected from hydrogen, hydroxyl, C1–C50 alkyl, C1–C50 alkoxy, C6–C40 aryloxy, C2–C50 alkenyl, C3–C20 cycloalkyl, C6–C40 aryl, C7–C50 aralkyl, C7–C50 alkaryl, C1–C20 alkylamino and dialkylamino, C6–C40 arylamino and diarylamino, C3–C30 heterocyclic containing one or more N, O, S, or P atoms, C2–C50 acyl, formyl, C7–C40 aroyl, cyano, halogen such as F, Br, I, or Cl, thiol, C1–C50 alkylthio, C6–C40 arylthio, amino, nitro, sulfonate having the formula $SO_3X$ wherein X is selected from sodium, C1–C50 alkyl, or C6–C40 aryl, alkyl sulfonyl, aryl sulfonyl, aminosulfonyl, hydroxycarbonyl, C1–C50 alkyloxycarbonyl and, C6–C40 aryloxycarbonyl, wherein the alkyl moieties in the $R_1$ groups may be linear or branched and each of the $R_1$ groups may be further substituted with appropriate groups; further wherein $R_3$, $R_4$, $R_5$, and $R_6$ are the same or different and are selected from hydrogen, hydroxyl, C1–C50 alkyl, C1–C50 alkoxy, C6–C40 aryloxy, C2–C50 alkenyl, C3–C20 cycloalkyl, C6–C40 aryl, C7–C50 aralkyl, C7–C50 alkaryl, C1–C20 alkylamino and dialkylamino, C6–C40 arylamino and diarylamino, C3–C30 heterocyclic containing one or more N, O, S, or P atoms, C2–C50 acyl, formyl, aroyl, cyano, halogen such as F, Br, I, or Cl, thiol, C1–C50 thioalkyl, C6–C40 thioaryl, amino, nitro, sulfonate having the formula $SO_3X$ wherein X is selected from sodium, C1–C50 alkyl, or C6–C40 aryl, alkyl sulfonyl, aryl sulfonyl, amino sulfonyl, hydroxy carbonyl, C1–C50 alkyloxy carbonyl and C6–C40 aryloxy carbonyl, wherein the alkyl moieties in the $R_3$, $R_4$, $R_5$, and $R_6$ groups may be linear or branched and each of the $R_3$, $R_4$, $R_5$, and $R_6$ groups may be further substituted where appropriate.

Preferred groups for R1 and R2 are C1–C20 alkyl, C6–C20 aryl, C7–C20 alkaryl, C3–C10 cycloalkyl, C2–C20 alkenyl, C3–C20 heterocyclyl, C2–C20 acyl and C7–C20 aroyl. Examples of satisfactory radicals for $R_1$, R2, $R_3$, $R_4$, $R_5$, and $R_6$ are linear or branched alkyls such as methyl, ethyl, propyl, butyl, pentyl, hexyl, heptyl, octyl, nonyl, decyl, dodecyl, 1,3-dimethyl butyl, 1,4-dimethyl pentyl, isopropyl, sec-butyl, 1-ethyl-3-methylpentyl, 1-methyl heptyl, and the like; aryls such as phenyl, naphthyl, anthracyl, tolyl, ethylphenyl, and the like; cycloalkyls such as cyclobutyl, cyclopentyl, cyclohexyl, cyclooctyl, and the like. Other examples include hydrogen, allyl and isobutenyl; 1,3,5-sym-triazinyl, 2-benzothiazolyl, 2-benzimidazolyl, 2-benzoxazolyl, 2-pyridyl, 2-pyrimidinyl, 2,5-thiadiazolyl, 2-pyrazinyl, adipyl, glutaryl, succinyl, malonyl, acetyl, acrylyl, methacrylyl, caproyl, 3-mercaptopropionyl, benzoyl, phthaloyl, terephthaloyl, aminocarbonyl, ethoxycarbonyl, formyl, and the like. These are merely exemplary radicals and are in no way intended to limit the scope of the invention.

In the reaction, according to the present invention, the metal catalysts are typically transition metals from Groups IB, IIB, VB, VIB, VIIB, and VIII of the periodic table. The metals may be in their ionic state or in the form of a metal salt. The catalysts may be used alone or in blends. Typically the metals include V, Nb, Ta, Cr, Mo, W, Mn, Tc, Re, Fe, Ru, Os, Co, Rh, Ir, Ni, Pd, Pt, Cu, Ag, Au, Zn, Cd, Hg, and their salts. Supported catalysts such as Pd/C, Pt/C, Ni/Al, Ru/C, Rh/C and the like, are also included. Some examples of preferred catalysts include, but are not limited to, Pt/C, Pd/C, Rh/C, Ru/C, nickel (II) oxide, cobalt phthalocyanine on carbon, and silver oxide.

The catalysts used in the present invention are typically present in amounts ranging from about 0.1 wt. % to about 20.0 wt %, based on the weight of the phenylenediamine starting material.

The catalysts of the present invention cause the conversion reaction in the process according to the present invention. It is advantageous to utilize solid catalysts in the reaction according to the present invention as there is ease in recovery of the solid catalysts, via filtration, and the solid catalysts can be reused in the process. There are also advantages with respect to environmental containment, and there is less likelihood that there will be contamination by the catalyst in the final isolate of quinonediimine. Further, the catalysts give high conversion and excellent selectivity.

The reaction, according to the present invention, takes place in either a homogeneous or two-phase solvent system. Water soluble organic solvents are used for the homogeneous reaction while water insoluble organic hydrocarbon solvents yield the two-phase system. The two-phase system also includes water. The two-phase oxidation system provides ease of separation of the organic components (both quinonediimine and solvent) from the spent aqueous layer. Organic aprotic solvents useable in the process of the present invention include, but are not limited to, ketones such as cyclohexanone, 4-methyl-2-pentanone (methyl isobutyl ketone), 5-methyl-2-hexanone, methyl ethyl ketone; aliphatic and aromatic hydrocarbons such as hexanes, heptanes, toluene, xylenes, nitrites such as acetonitrile; halogenated solvents such as chloroform, dichloromethane, carbon tetrachloride; water soluble solvents such as dimethyl sulphoxide, N-methyl-2-pyrrolidone, sulfolane, dimethylformamide; esters such as ethyl acetate; ethers such as 1,4-dioxan, alcohols such as methanol, and mixtures thereof.

As with the catalysts, the solvents, when recovered from the product, may be recycled and reused in the reaction.

When water is present in the reaction, it is typically present in amounts of up to 75 wt %, based upon the weight of the total reaction mixture. Water can be present as the sole solvent or it can be combined with other water soluble or water insoluble organic solvents.

When utilizing a water soluble salt of a metal catalyst in the reaction according to the present invention, it is desirable to utilize a two-phase solvent system. The use of a two-phase solvent system with the water soluble metal catalysts permits ease of separation of the catalyst from the desired end product as the end product is present in the organic phase while the catalyst is present in the aqueous phase. Once again, the catalyst and aqueous solvent can be recycled back into the reaction.

The initial phenylenediamine concentration may range in amounts of from about 1% to 100% w/v. Preferably, the initial phenylenediamine concentration ranges from about 25% to about 60% w/v.

The present reaction may take place at temperatures from about 0° C. to about 150° C., preferably from about 25° C. to about 70° C.

A phase-transfer catalyst may be utilized to accelerate the rate of reaction with the above mentioned metal catalysts. With water immiscible solvents it is advantageous to utilize a phase transfer catalyst to accelerate the rate of reaction in the process of the present invention. Phase transfer catalysts useable in the present invention include, but are not limited to, quaternary ammonium salts, such as tetramethyl ammonium hydroxide, tetra alkyl ammonium halides, tetra-N-butyl ammonium bromide, tetra-N-butyl ammonium chloride, benzyltriethyl ammonium chloride; phosphonium salts such as bis[tris(dimethylamino)phosphine]iminium chloride; crown ethers and polyethylene glycols.

The phase transfer catalyst can be added directly to the reaction mixture or it can be dissolved in one of the reagents such as phenylenediamine. The phase transfer catalyst may also be dissolved in a solvent used in the process or in water before addition to the reaction mass.

Another means by which the rate of reaction may be increased is by increasing the stirring or mixing rate in the reaction. By increasing the stirring or mixing, the reaction rate may be effectively adjusted to proceed at a faster pace when necessary.

Other means of increasing the reaction rate include increasing the temperature of the reaction, increasing the pressure at which the reaction takes place and by increasing the amount of catalyst used.

Additionally, the addition of basic pH adjusting agents, such as triethylamine, can increase the reaction rate and also provide increased selectivity for the desired quinonediimine end product.

Further, the reaction can utilize a combination of more than one phenylenediamine starting material to produce a product containing a mixture of quinonediimines.

Also, the reaction may be stopped prior to completion thereby producing a product comprising a mixture of phenylenediamine and quinonediimine. By adjusting the amount of catalyst, adjusting the amount of pH adjusting agents, and/or adjusting the amount of oxygen present in the reaction, for example, one can obtain highly specific blends of phenylenediamine and quinonediimine. Depending upon the particular use of the product, such blends may provide better results than a product with high amounts of quinonediimine.

The present invention can be more clearly illustrated by the following examples.

EXAMPLE 1

A mixture of N-1,3-dimethylbutyl-N'-phenyl-p-phenylenediamine (Santoflex® 6PPD, 5 g, 0.019 moles), methanol (200 mL), triethylamine (2 mL), water (2 mL) and catalyst was charged to an autoclave. The reaction mixture was stirred and the autoclave purged with oxygen and then charged to 30 psig oxygen at 20–25° C. The reaction mixture was heated to 50° C. and maintained at 50° C. until the reaction was complete. As the reaction progressed, the oxygen pressure dropped. When the pressure dropped to about 20 psig, more oxygen was charged to the reactor to bring the pressure back to 30 psig. The reaction time was counted from the moment oxygen was initially charged to the autoclave. When very little or no oxygen uptake was detectable, the mixture was filtered to separate the catalyst.

The reaction times and product composition of the resulting mixtures are tabulated in the following table. In most cases high conversions to the desired quinone-diimine product of N-1,3-dimethylbutyl-N'-phenyl-p-phenylenediimine (6QDI) were obtained. In some reactions, the reaction was not complete and hence the mixture indicated presence of unreacted starting material Santoflex® 6PPD. Simply further continuing the reaction can complete these reactions. When the catalyst is heterogeneous, the reaction mixture can be filtered to separate the product from the catalyst. Concentration of the filtered reaction mixture can lead to the desired product, 6QDI in very high yields.

In the examples listed in the following table, the reaction mixture was analyzed when there was no more consumption of oxygen or very little uptake of oxygen thereby indicating completion of the reaction. However, this method of judging the completion of reaction was not always reliable. Hence, in some reactions, there was unreacted starting material present. At the same time, when reactions were fully complete, actual reaction time could be lower than listed in the table 1.

Analysis indicated disappearance of Santoflex® 6PPD and formation of the corresponding quinone-diimine in high selectivity. The results of HPLC area % analysis are summarized in the following table 1.

Catalysts used for the run numbers 1–4 had approximately 50% water. As such, on the dry weight basis, the weight of catalyst would be roughly half the amount. For example, 0.5 g would in turn be 0.25 g and so on.

Various isolation techniques well known in the art may be used to isolate the product according to the present invention, such isolation techniques include, but are not limited to, filtration and concentration. The catalyst and solvent recovered from the reaction can be recycled and reused in subsequent reactions.

TABLE 1

| No. | Catalyst used | Catalyst weight | Rxn Time Hours | HPLC Area % Product 6QDI | HPLC Area % Starting Material Santoflex 6PPD |
|---|---|---|---|---|---|
| 1 | 3% Platinum on Carbon | 0.5 g | 2.8 | 92.3 | 3 |
| 2 | 3% Palladium on Carbon | 1.5 g | 3.5 | 97.6 | 0 |
| 3 | 5% Rhodium on Carbon | 1.3 g | 1.6 | 97.1 | 0 |
| 4 | 5% Ruthenium on Carbon | 1.2 g | 2.7 | 82.2 | 14.9 |
| 5 | Nickel (II) Oxide | 0.5 g | 2.3 | 87 | 11.9 |
| 6 | Cobalt (III) Oxide | 0.5 g | 2.1 | 97.9 | 0.6 |
| 7 | 5 wt % Cobalt Phthalocyanine on Carbon | 0.5 g | 2.1 | 91.5 | 2.8 |
| 8 | Silver Oxide | 0.5 g | 3.3 | 91.7 | 3.3 |

A comparison of the following three examples indicates the advantages of adding pH adjusting agents, such as triethylamine, on the rate of reaction and the selectivity of the desired product 6QDI. In the following examples the weight of catalyst used is wet weight, which has about 50% water. Hence the dry weight of catalyst used would be half the amount. For example, in case of catalyst weight of 0.500 g, the dry weight of catalyst would be 0.25 g and so on.

These examples were done under identical conditions and the same raw materials were used in all the reactions to avoid variation from batch to batch and for better comparison. The reactions were not taken to full completion and hence HPLC analysis indicated presence of unreacted starting material Santoflex® 6PPD. Simply further continuing the reaction can complete these reactions.

EXAMPLE 2

This example teaches the effect of triethylamine to increase the rate of reaction and for better selectivity for the desired product quinone-diimine.

In accordance with procedure set forth in Example 1, a mixture of N-1,3-dimethylbutyl-N'-phenyl-p-phenylenediamine (Santoflex® 6PPD, 10.0 g, 0.038 moles), methanol (200 mL), triethylamine (2 mL), and catalyst, 3% Pt/C (0.500 g), was charged to an autoclave. The reaction progress was monitored by taking samples over a period of time and analyzing by HPLC for the product 6QDI and for the starting material Santoflex® 6PPD. The following table 2 summarizes the results.

TABLE 2

| Sample No. | Time Hours | HPLC area % Product 6QDI | HPLC area % starting material Santoflex 6PPD |
|---|---|---|---|
| 1 | 0.5 | 9.9 | 89.7 |
| 2 | 1 | 18.1 | 81.7 |
| 3 | 1.5 | 41.6 | 58 |
| 4 | 3.25 | 56.6 | 42.6 |
| 5 | 5.5 | 65.6 | 32.9 |
| 6 | 6.5 | 66.8 | 31.8 |

Addition of triethylamine is helpful since the selectivity for the desired product 6QDI is very high and rate of reaction is exceptionally high too.

EXAMPLE 3

This example teaches the effect of addition of triethylamine and water to increase the rate of reaction and for better selectivity for the desired product quinone-diimine.

In accordance with procedure set forth in Example 1, a mixture of N-1,3-dimethylbutyl-N'-phenyl-p-phenylenediamine (Santoflex® 6PPD, 10.0 g, 0.038 moles), methanol (200 mL), triethylamine (2 mL), water (2 mL) and catalyst, 3% Pt/C (0.500 g), was charged to an autoclave. The reaction progress was monitored by taking samples over a period of time and analyzing by HPLC for the product 6QDI and for the starting material Santoflex® 6PPD. The following table 3 summarizes the results.

TABLE 3

| Sample No. | Time Hours | HPLC area % Product 6QDI | HPLC area % starting material Santoflex 6PPD |
|---|---|---|---|
| 1 | 0.5 | 25.5 | 68.6 |
| 2 | 1 | 38.5 | 61.3 |
| 3 | 1.5 | 38.2 | 59.8 |
| 4 | 2 | 47.9 | 49.4 |
| 5 | 3 | 57.1 | 42.5 |
| 6 | 4 | 58 | 36.7 |
| 7 | 5 | 69.1 | 30.1 |
| 8 | 6 | 74.2 | 24 |

Addition of triethylamine and water is helpful since the selectivity for the desired product 6QDI is very high and rate of reaction is exceptionally high also. This example also indicates that water in the reaction does not have an adverse effect on the reaction.

EXAMPLE 4

The reaction will proceed in the absence of a pH adjusting agent as demonstrated in the following example. In this manner, a product comprising a mixture of phenylenediamine and quinonediimine can be produced, or the reaction can be allowed to go to completion if desired.

In accordance with procedure set forth in Example 1, a mixture of N-1,3-dimethylbutyl-N'-phenyl-p-phenylenediamine (Santoflex® 6PPD, 10.0 g, 0.038 moles), methanol (200 mL), and catalyst, 3% Pt/C (0.500 g), was charged to an autoclave. The reaction progress was monitored by taking samples over a period of time and analyzing by HPLC for the product 6QDI and for the starting material Santoflex® 6PPD. The following table 4 summarizes the results.

TABLE 4

| Sample No. | Time Hours | HPLC area % Product 6QDI | HPLC area % starting material Santoflex 6PPD |
|---|---|---|---|
| 1 | 1 | 7.6 | 86.1 |
| 2 | 2 | 27 | 65.6 |
| 3 | 3 | 33.7 | 53.2 |
| 4 | 4 | 39.1 | 49.2 |
| 5 | 5 | 46.4 | 37.5 |
| 6 | 5.6 | 46.9 | 35.1 |
| 7 | 7 | 49 | 24.2 |

In this experiment, HPLC analysis indicated formation of few new peaks other than the starting material Santoflex® 6PPD and the product quinone-diimine (6QDI) compounds. The formation of undesired byproducts, in turn, reduced the selectivity of the formation of the desired product 6QDI.

Even without the presence of triethylamine, the reaction proceeded, although at a slower rate than with triethylamine.

The comparison of the following two examples further illustrates the advantages of adding pH adjusting agents, such as triethylamine, on the rate of reaction and the selectivity of desired product 6QDI. In the following examples the weight of catalyst used is wet weight, which has about 50% water. Hence the dry weight of catalyst used would be half the amount. For example, in case of catalyst weight of 1.550 g, the dry weight of catalyst would be 0.775 g and so on.

EXAMPLE 5

In accordance with procedure set forth in Example 1, a mixture of N-1,3-dimethylbutyl-N'-phenyl-p-phenylenediamine (Santoflex® 6PPD, 5.0 g, 0.019 moles), methanol (200 mL), triethylamine (2 mL), water (2 mL) and catalyst 3% Pt/C (1.550 g) was charged to an autoclave. The reaction progress was monitored by taking samples over a period of time and analyzing by HPLC for the product 6QDI and for the starting material Santoflex® 6PPD. The first sample taken after 0.5 hrs was analyzed by HPLC area % and found to contain 99.3% 6QDI. The second sample after 1 hr reaction time when analyzed by HPLC area % was found to contain 99.4% 6QDI. This was a clear indication that the reaction was done. The reaction mixture was filtered to remove the catalyst and the filtrate was concentrated to remove volatiles. The resulting dark reddish colored liquid was identified to be the corresponding N-1,3-dimethylbutyl-N'-phenyl-quinonediimine (6QDI) and isolated in almost quantitative yields.

EXAMPLE 6

In accordance with the procedure set forth in Example 1, and under the same conditions as in example 5 except as to the addition of triethylamine and water, this experiment was carried out. A mixture of N-1,3-dimethylbutyl-N'-phenyl-p-phenylenediamine (Santoflex® 6PPD, 5.0 g, 0.019 moles), methanol (200 mL), and catalyst, 3% Pt/C (1.550 g), was charged to an autoclave. The reaction progress was monitored by taking samples over a period of time and analyzing by HPLC for the product 6QDI and for the starting material Santoflex® 6PPD. The following table 5 summarizes the results of HPLC area % analysis. These results clearly indicate that the reaction without triethylamine and water is slower than the reaction with triethylamine and water present as demonstrated in example 5 where the reaction was done in 30 minutes.

TABLE 5

| Sample No. | Time Hours | HPLC area % Product 6QDI | HPLC area % starting material Santoflex 6PPD |
|---|---|---|---|
| 1 | 0.5 | 69.9 | 23.9 |
| 2 | 1 | 85.1 | 11.3 |
| 3 | 1.5 | 91.6 | 5.3 |

An increased amount of catalyst in the process of Example 6 can be seen to produce an increased reaction rate compared to Example 4.

The quinonediimines prepared by the process of the present invention exhibit multiple activities in vulcanized elastomers. These activities include long term antioxidant activity, along with antiozonant capacity. In fact, the antioxidant capacity of these antidegradants persists even after the vulcanizate has been extracted with solvents. In addition, quinonediimines provide these benefits without the negative effect on scorch generally associated with para-phenylenediamine antidegradants common to the industry. Summary of the activities of these compounds in rubber can be found in the literature. (Cain, M. E. et al., *Rubber Industry*, 216–226, 1975).

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the invention, it is claimed:

1. A process for preparing a quinonediimine by reacting a corresponding phenylenediamine with oxygen in the presence of a metal catalyst or a salt thereof.

2. The process of claim 1 wherein the metal catalyst is a supported metal catalyst, a transition metal catalyst, a salt of a transition metal catalyst, or mixtures thereof.

3. The process of claim 2 wherein the metal catalyst is present in an amount of from about 0.1 wt. % to about 20.0 wt %, based upon the weight of the phenylenediamine starting material.

4. The process of claim 1 wherein the phenylenediamine is an ortho- or para-phenylenediamine of the following Formula Ia or Ib:

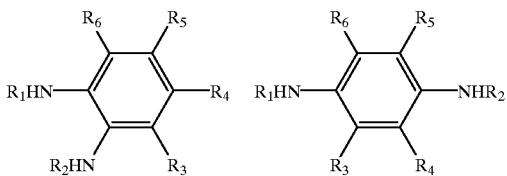

wherein $R_1$ and $R_2$ are independently selected from hydrogen, hydroxyl, alkyl, alkoxy, aryloxy, alkenyl, cycloalkyl, aryl, aralkyl, alkaryl, alkylamino, arylamino, heterocycle, acyl, formyl, aroyl, cyano, halogen, thiol, alkylthio, arylthio, amino, nitro, sulfonate, alkyl sulfonyl, aryl sulfonyl, amino sulfonyl, hydroxy carbonyl, alkyloxycarbonyl and aryloxycarbonyl, wherein the alkyl moieties in the $R_1$ and $R_2$ groups may be linear or branched and each of the $R_1$ and $R_2$ groups may be further substituted; further wherein $R_3$, $R_4$, $R_5$, and $R_6$ are the same or different and are selected from hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, alkylthio, arylthio, amino, nitro, sulfonate, alkyl sulfonyl, aryl sulfonyl, aminosulfonyl, hydroxycarbonyl, alkyloxycarbonyl and aryloxycarbonyl, wherein the alkyl moieties in the $R_3$, $R_4$, $R_5$, and $R_6$ groups may be linear or branched and each of the $R_3$, $R_4$, $R_5$, and $R_6$ groups may be further substituted and further wherein the resulting corresponding quinonediimine is of the following Formula IIa or IIb:

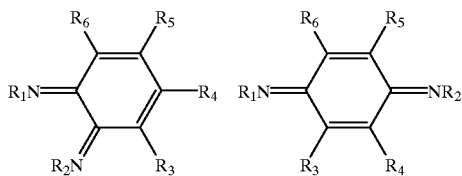

wherein $R_1$, $R_2$, $R_3$, $R_4$, $R_5$ and $R_6$ are the same as in the compound of Formula I.

5. The process of claim 4 wherein $R_1$, $R_2$, $R_3$, $R_4$, $R_5$ and $R_6$ are selected from phenyl, tolyl, naphthyl, 1,3-dimethylbutyl, 1,4-dimethylpentyl, isopropyl, sec-butyl, cyclohexyl, 1-ethyl-3-methylpentyl, 1-methylheptyl, and hydrogen.

6. The process of claim 4 wherein $R_1$=phenyl, $R_2$=1,3-dimethylbutyl, $R_3$=hydrogen, $R_4$=hydrogen, $R_5$=hydrogen and, $R_6$=hydrogen.

7. The process of claim 4 wherein the phenylenediamine is a para-phenylenediamine.

8. The process of claim 7 wherein $R_1$ and $R_2$=sec-butyl and $R_3$, $R_4$, $R_5$ and $R_6$=hydrogen.

9. The process of claim 7 wherein $R_1$ and $R_2$=1,4-dimethylpentyl and $R_3$, $R_4$, $R_5$ and $R_6$=hydrogen.

10. The process of claim 1 which further comprises addition of a basic pH adjusting agent to the reaction.

11. The process of claim 10 wherein the basic pH adjusting agent is triethylamine.

12. The process of claim 11 wherein the reaction further includes water.

13. The process of claim 1 wherein the reaction takes place in the presence of a solvent.

14. The process of claim 13 wherein the solvent is selected from ketones, alcohols, nitriles, aliphatic hydrocarbons, aromatic hydrocarbons, halogenated hydrocarbons, water, and mixtures thereof.

15. The process of claim 14 wherein the solvent is an alcohol.

16. The process of claim 15 wherein the alcohol solvent is selected from methyl alcohol, ethyl alcohol, and isopropyl alcohol.

17. The process of claim 14 wherein the solvent comprises water in an amount of up to about 75 wt %, based on the weight of the total reaction mass.

18. The process of claim 13 which further comprises addition of a phase transfer catalyst to the reaction to increase the reaction rate.

19. The process of claim 18 wherein the phase transfer catalyst is selected from quaternary ammonium salts, phosphonium salts, crown ethers, and polyethylene glycols.

20. The process of claim 1 wherein the reaction takes place at a temperature of between about 0° C. and about 150° C.

21. The process of claim 1 wherein the reaction rate may be further increased by increasing the mixing rate in the reaction.

22. The process of claim 1 wherein the reaction rate may be increased by increasing the amount of catalyst used in the reaction.

23. A process for preparing a quinonediimine by reacting the corresponding phenylenediamine with oxygen in the presence of a metal catalyst or metal salt catalyst wherein the phenylenediamine is an ortho- or para-phenylenediamine of the following Formula Ia or Ib:

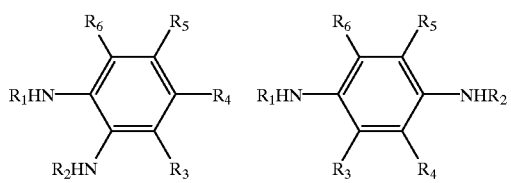

wherein $R_1$ and $R_2$ are independently selected from hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, alkylthio, arylthio, amino, nitro, sulfonate, alkyl sulfonyl, aryl sulfonyl, amino sulfonyl, hydroxy carbonyl, alkyloxy carbonyl, and, aryloxy carbonyl, wherein the alkyl moieties in the $R_1$ and $R_2$ groups may be linear or branched and each of the $R_1$ and $R_2$ groups may be further substituted; further wherein $R_3$, $R_4$, $R_5$ and $R_6$, are the same or different and are selected from hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, alkylthio, arylthio, amino, nitro, sulfonate, alkyl sulfonyl, aryl sulfonyl, amino sulfonyl, hydroxy carbonyl, alkyloxycarbonyl and aryloxycarbonyl, wherein the alkyl moieties in the $R_3$, $R_4$, $R_5$ and $R_6$ groups may be linear or branched and each of $R_3$, $R_4$, $R_5$ and $R_6$ groups may be further substituted and further wherein the resulting corresponding quinonediimine is of the following Formula IIa or IIb:

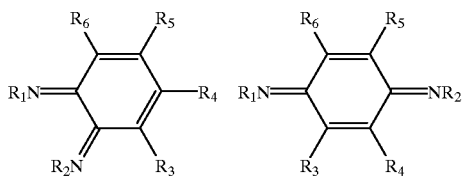

wherein $R_1$, $R_2$, $R_3$, $R_4$, $R_5$ and $R_6$ are the same as in the compound of Formula Ia or Ib wherein the reaction takes place in a homogenous solvent system or in a two-phase solvent system comprising a water insoluble organic solvent and water.

24. The process of claim 23 wherein the reaction takes place in a homogeneous solvent system and the solvent is selected from water soluble organic solvents.

25. The process of claim 24 wherein the water soluble organic solvent is an alcohol.

26. The process of claim 25 wherein the reaction further includes water.

27. The process of claim 23 wherein the reaction takes place in a two-phase solvent system comprising a water insoluble organic solvent and water.

28. The process of claim 27 which further comprises addition of a phase transfer catalyst to the reaction to increase the reaction rate.

29. The process of claim 28 wherein the phase transfer catalyst is selected from quaternary ammonium salts, phosphonium salts, crown ethers, and polyethylene glycols.

30. The process of claim 23 wherein the metal catalyst is a supported metal catalyst, a transition metal catalyst, a salt of a transition metal catalyst, or mixtures thereof.

31. The process of claim 30 wherein the catalyst is selected from Pt/C, Pd/C, Rh/C, Ru/C, nickel (II) oxide, cobalt (III) oxide, cobalt phthalocyanine on carbon, silver oxide, or mixtures thereof.

32. The process of claim 23 wherein $R_1$, $R_2$, $R_3$, $R_4$, $R_5$ and $R_6$, are selected from phenyl, tolyl, naphthyl, 1,2-dimethylbutyl, 1,4-dimethylpentyl, isopropyl, sec-butyl, cyclohexyl, 1-ethyl-3-methylpentyl, 1-methylheptyl, and hydrogen.

33. The process of claim 23 where $R_1$=phenyl, $R_2$=1,3-dimethylbutyl, $R_3$=hydrogen, $R_4$=hydrogen, $R_5$=hydrogen, and $R_6$=hydrogen.

34. The process of claim 23 wherein the phenylenediamine is a para-phenylenediamine.

35. The process of claim 23 wherein the phenylenediamine component is a mixture of two or more pheylenediamines.

36. The process of claim 35 wherein the mixture of phenylenediamines comprises N-1,3-dimethylbutyl-N'-phenyl-p-phenylenediamine.

37. The process of claim 23 wherein the reaction is stopped prior to completion to produce a product comprising a mixture of the phenylenediamine and the quinonediimine.

* * * * *